United States Patent
Ryoo et al.

(10) Patent No.: US 6,875,822 B2
(45) Date of Patent: Apr. 5, 2005

(54) PROCESS FOR PREPARING TRITYLATED POLYSTYRENE RESIN

(75) Inventors: Sun-Jong Ryoo, Seoul (KR); Tae-kyung Lee, Seoul (KR); Ju-Han Kim, Seoul (KR)

(73) Assignee: Beadtech, Inc., Seoul (KR)

( * ) Notice: Subject to any disclaimer, the term of this patent is extended or adjusted under 35 U.S.C. 154(b) by 0 days.

(21) Appl. No.: 10/301,811

(22) Filed: Nov. 22, 2002

(65) Prior Publication Data

US 2003/0105243 A1 Jun. 5, 2003

(30) Foreign Application Priority Data

Nov. 27, 2001 (KR) ................................. 10-2001-0074387

(51) Int. Cl.⁷ ................................................. C08F 8/18
(52) U.S. Cl. ................................ 525/359.6; 525/333.4; 525/359.1; 525/359.3
(58) Field of Search .......................... 525/333.4, 359.1, 525/359.3, 359.6

(56) References Cited

U.S. PATENT DOCUMENTS

| | | | |
|---|---|---|---|
| 4,085,261 A | | 4/1978 | Patchornik et al. |
| 5,084,522 A | * | 1/1992 | Frechet ..................... 525/333.4 |
| 5,563,220 A | | 10/1996 | Webber et al. |
| 5,922,890 A | | 7/1999 | Bleicher |

OTHER PUBLICATIONS

Fréchet, Jean M. J. et al. "Use of Polymers as Protecting Groups in Organic Synthesis." *Tetrahedron Letters*. No. 35, pp. 3055–3056, 1975.

Cohen, B. J. et al. "Organic Synthesis Involving Multipolymer Reactions. Polymeric Trityllithium." *Journal of the American Chemical Society*. vol. 99, No. 12, pp. 4165–4167, 1977.

Cohn, B. J. et al. "'Wolf and Lamb' Reactions: Equilibrium and Kinetic Effects in Multipolymer Systems." *Journal of the American Chemical Society*. vol. 103, No. 25, pp. 7620–7629, 1981.

Borhan, Babak et al. "Suspension Copolymerization as a Route to Trityl–Functionalized Polystyrene Polymers." *Journal of Organic Chemistry*. vol. 60, pp. 7375–7378. 1995.

Orosz, György et al. "Simple and Efficient Synthesis of 2–Chlorotritylchloride Resin." *Tetrahedron Letters*. No. 39, pp. 3241–3242, 1998.

Hidai, Yuko et al. "Total Synthesis of Polyamine Toxin HO–416b Utilizing the 2–Nitrobenzenesulfonamide Protecting Group." *Tetrahedron Letters*. No. 40, pp. 4711–4714, 1999.

Manzotti, Raffaella et al. "Improved Synthesis of (4–ethenylphenyl) diphenyl methanol and its Application in the Preparation of Trityl Functionalized Polystyrene Resin Containing Tetrahydrofuran derived Cross–linker." *Tetrahedron Letters*. No. 41, pp. 8417–8420, 2000.

* cited by examiner

*Primary Examiner*—Fred Teskin
(74) *Attorney, Agent, or Firm*—Nath & Associates PLLC; Gary M. Nath; Jerald L. Meyer

(57) ABSTRACT

The present invention relates to a process for preparing tritylated polystyrene resin. More particularly, the present invention is directed to a process for preparing tritylated polystyrene resins, comprising a step for tritylating polystyrene by reacting polystyrene resin with benzophenone dichloride or substituted benzophenone dichloride to introduce trityl group on the benzene moiety of the polystyrene.

8 Claims, No Drawings

PROCESS FOR PREPARING TRITYLATED POLYSTYRENE RESIN

TECHNICAL FIELD

The present invention relates to a process for preparing tritylated polystyrene resin. More particularly, the present invention is directed to a process, comprising a step for tritylating polystyrene by reacting polystyrene resin with benzophenone dichloride or substituted benzophenone dichloride to introduce trityl group on the benzene moiety of the polystyrene.

BACKGROUND ART

Since Mr. R. B. Merrifield disclosed the theory of solid phase peptide synthesis, various resins for synthesizing peptide have been developed.

Chloromethyl polystyrene resin disclosed by Merrifield is important as the first resin used for solid phase peptide synthesis. However, chloromethyl polystyrene resin has been applied to very limited cases of solid phase peptide syntheses because strong acid such as hydrofluoric acid(HF) are required to recover synthesized peptides.

Therefore, Wang resin having a structure of 4-alkoxybenzyl alcohols has been developed in order to overcome the drawback of chloromethyl polystyrene resin.

Wang resin has been widely employed in solid phase peptide syntheses because it allows synthesized peptide to be recovered under more weak acid conditions than chloromethyl polystyrene resin.

However, Wang resin is not suitable to be used in obtaining peptide products with their protecting groups retained, because the protecting groups combined on their side chains are eliminated during the separation process of synthesized peptides from Wang resin.

In addition, Wang resin has the drawbacks that catalyst for activating alcohol group is required to combine a first amino acid to resin, that racemization may be appeared or that diketopiperazine may be formed.

Therefore, tritylated polystyrene resin of the present invention has been developed in order to overcome the above drawbacks of Merrifield resin and Wang resin.

Peptides can be separated from solid phase under weak acid condition by using tritylated polystyrene resin, so that the protecting groups combined on their side chains can be retained during the separation.

In addition, catalysts are not required to introduce a first amino acid on the substrate resin because the chemical structure of trityl group is activated in itself. Furthermore, the formation of diketopiperazine and racemization can be advantageously suppressed during peptide synthesis process because trityl group causes great steric hindrance effect.

Meanwhile, trityl group can be introduced to polystyrene resin by introducing linkers having trityl group to the resin after the preparation of the polystyrene resin, or by polymerizing styrene monomers having trityl group.

J. M. J. Frechet et al. disclosed a process introducing bezophenone group on polystyrene resin by using benzoyl chloride and then, synthesizing tritylated polystyrene resin by using Grignard reagent(Tetrahedron Letters No.35, pp3055–3056, 1975).

U.S. Pat. No. 5,922,890 disclosed a process for preparing tritylated resin wherein dichlorobenzo phenone is reacted with 4-tolylmagnesium bromide, and oxidized to give 4-(bis-(4-chlorophenyl)-hydroxymethyl)benzoic acid, and then 4-(bis-(4-chlorophenyl)-hydroxymethyl)benzoic acid thus obtained is combined to resin having amino group to give the tritylated resin.

G. Orosz has developed a process for preparing 2-chlorotrityl polystyrene resin in which 2-chlorobenzophenone group is introduced to the benzene moiety of polystyrene by reacting the polystyrene with 2-chlorobenzoyl chloride and then the resulted product is reacted with phenyl lithium to give 2-chlorotrityl polystyrene resin(Tetrahedron Letters No.39, pp3241–3242, 1998).

However, the processes described in the above require hard reaction conditions and enormous manufacturing cost because all of them employ strong basic Grignard reagents or highly reactive organo metallic compounds.

Especially, the above process for preparing tritylated resin requires the use of organo metallic compounds, which are hard to handle during large-scale process. Also, this process is too long and complicated so that the production cost can not but increase.

Therefore, a process for preparing tritylated polystyrene resin used for synthesizing peptides, which does not require the use of organo metallic compounds and not require complicated steps, has been anticipated in this field for a long time.

DISCLOSURE OF INVENTION

Therefore, the object of the present invention is to provide a process for preparing tritylated polystyrene resin wherein polystyrene resin is reacted with unsubstituted or substituted benzophenone dichloride to give tritylated polystyrene resin through one-step reaction which requires less production cost and can be controlled easily.

The above object of the present invention can be achieved by providing a process for preparing tritylated polystyrene resins(III), comprising a step for tritylating polystyrene by reacting polystyrene resin(II) with benzophenone dihalide (I), wherein X is hydrogen or halogen, Y is hydrogen, halogen, $C_{1-4}$ alkyl or alkoxy and A is halogen.

Reaction Scheme 1

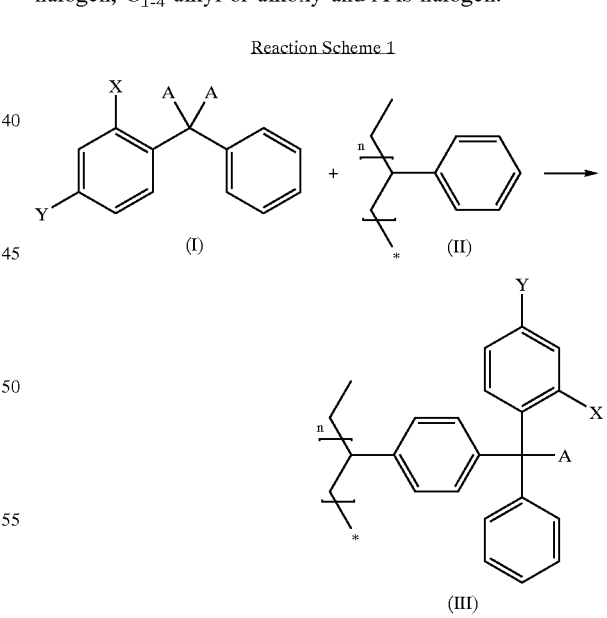

Benzophenone dihalide or substituted benzophenone dihalide used in the present invention can be prepared by halogenating benzophenone or substituted benzophenone, as represented in Reaction Scheme 2.

However, the present invention is not limited to the above, the starting material of the present invention can be prepared by conventional various methods already known to a public.

Reaction Scheme 2

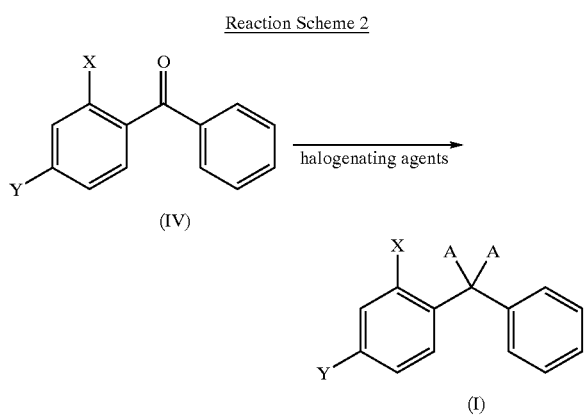

Halogenating agents used for the reaction scheme 2 can be selected from the group consisting of chlorinating agents, brominating agents or iodizing agents.

The chlorinating agents can be used for the reaction scheme 2 include $PCl_3$, $PCl_5$, $COCl_2$ and $SOCl_2$. Preferably, upon considering reaction efficiency and economical benefits, $PCl_5$ or the mixture thereof can be used.

The appropriate amount of $PCl_5$ is 0.5 mol to 2.0 mol, more preferably 0.5 mol to 1.5 mol per one mole of benzophenone or substituted benzophenone.

The brominating agents used for the reaction of Scheme 2 include $PBr_3$, $PBr_5$, $SOBr_2$ and so on.

The iodizing agents used for the reaction of Scheme 2 include $PI_3$ and so on.

The halogenation process of Reaction Scheme 2 can be proceeded preferably at high temperature, more preferably at 50° C. to 200° C., most preferably 70° C. to 170° C. upon considering the reaction rate and stability.

The reaction time is 30 minutes to 6 hours, preferably 1 hour to 4 hours.

As the reaction is proceeded, the peak of $^{13}C$ NMR which stands for carbonyl carbon contained in benzophenone or substituted benzophenone(IV) shifted into that of aliphatic carbon contained in benzophenone dihalide or substituted benzophenone dihalide(I).

Therefore, the preparation of benzophenone dihalide or substituted benzophenone dihalide can be confirmed by monitoring the shift of the peak of $^{13}C$ NMR.

The tritylated polystyrene resin(III) of the present invention can be prepared by reacting the benzophenone dihalide or substituted benzophenone dihalide(I) with polystyrene resin(II).

The above is a kind of Friedel-Crafts reaction in which the benzophenone dihalide or substituted benzophenone dihalide(I) acts as an alkylating agents.

The Lewis acid catalysts commonly used in the Friedel-Crafts reaction can also be used in the present invention. The Lewis acid catalysts used for the present invention include $AlBr_3$, $AlCl_3$, $BCl_3$, $BF_3$, $BiCl_3$, $GaCl_3$, $FeCl_3$, $SbCl_3$, $SbCl_5$, $SnCl_4$, $TeCl_4$, $ZnCl_2$, $ZrCl_4$ and so on, preferably anhydrous forms thereof.

The appropriate amount of Lewis acid catalysts of the present invention is 0.1 g to 10 g, more preferably 0.5 g to 5 g per one gram of polystyrene resin.

There is no limitation to the amount of benzophenone dihalide or substituted benzophenone dihalide(I) used in the present invention.

However, the appropriate amount of benzophenone dihalide or substituted benzophenone dihalide(I) is 0.1 g to 10 g, more preferably 1 g to 10 g per one gram of polystyrene resin in consideration of reaction efficiency and economical aspect.

The solvent commonly used in the Friedel-Crafts reaction can also be used for the present invention.

In addition, the solvents used for the present invention include halogenated solvents such as dichloromethane, chloroform, carbon tetrachloride, 1,2-dichloroethane, o-dichlorobenzene, m-dichlorobenzene, p-dichlorobenzene and so on, nitrificated solvents such as nitromethane, nitrobenzene and so on, or carbon disulfide and so on.

These solvents can be used individually or as mixture thereof.

There is no limitation in the reaction temperature of the present invention and however, it is preferably 0° C. to 150° C., more preferably 0° C. to 100° C.

The reaction time is 10 minutes to 48 hours, preferably 1 hour to 24 hours upon considering the reactivity of each reagents and the reaction productivity.

Meanwhile, tritylated halide resin can be prepared by halogenating substituted tritylated alcohol resin at room temperature or at high temperature.

The chlorinating agents used in the halogenation include acetyl chloride, trimethylsilyl chloride, $COCl_2$(phosgene), $SOCl_2$(thionyl chloride) and so on.

Hereinafter, the present invention is further described by the way of illustration only in the following non-limiting examples.

BEST MODE FOR CARRYING OUT THE INVENTION

EXAMPLE 1

Preparation of benzophenone dichloride 22.9G of $PCl_5$ and 20.0 g of benzophenone were placed in a 100 ml 3 neck round bottom flask in which a mechanical stirrer and a thermometer were installed, and refluxed for two hours using heating mantle and cooled to room temperature.

40 Ml of dicholoromethane was added to the resultant solution followed by transferring to 250 ml Erlenmeyer flask. The resultant solution was cooled to 0° C. and 40 ml of distilled water was added thereto.

The resultant solution was transferred to a separatory funnel, the phase of dichloromethane separated and washed twice with 40 ml distilled water.

The solvent in the resultant phase of dichloromethane was evaporated in rotary evaporator to give 24.3 g(93% purity, 87% yield) of benzophenone dichloride as a colorless liquid.

EXAMPLE 2

Preparation of 2-Chlorobenzophenone dichloride

The reaction was proceeded by the method described in Example 1. 270.8G of $PCl_5$ and 281.5 g of 2-chlorobenzophenone were placed in 1L 3 neck round bottom flask in which a mechanical stirrer and a thermometer were installed.

The resultant mixture was purified by the same method as described in Example 1 to give 338 g(97% purity, 93% yield) of 2-chlorobenzophenone dichloride as a yellow liquid.

EXAMPLE 3

Preparation of 4-Chlorobenzophenone dichloride

The reaction was proceeded by the method described in Example 1. 21.6G of $PCl_5$ was reacted with 20.8 g of 4-chlorobenzophenone to give 24.6 g(purity 98%, yield 89%) of 4-chlorobenzophenone dichloride as a colorless liquid.

EXAMPLE 4
Preparation of 4-Methylbenzophenone dichloride

The reaction was proceeded by the method described in Example 1. 20.8G of $PCl_5$ was reacted with 19.6 g of 4-methylbenzophenone to give 22.9 g(purity 87%, yield 79%) of 4-methylbenzophenone dichloride as a pale yellow liquid.

EXAMPLE 5
Preparation of 4-methoxybenzophenone dichloride

The reaction was proceeded by the method described in Example 1. 10.4G of $PCl_5$ was reacted with 10.6 g of 4-methoxybenzophenone to give 10.6 g(purity 89%, yield 70%) of 4-methoxybenzophenone dichloride as a tan liquid.

EXAMPLE 6
Preparation of tritylated alcohol polystyrene resin 4.0G of spherical polystyrene resin crosslinked with 1 wt % of divinylbenzene and 40 ml of dichloromethane were placed in a 250 ml 3 neck flask in which a mechanical stirrer and a thermometer were installed.

A solution of 6.6 g of $AlCl_3$ in 15 ml of o-dichlorobenzene was added with stirring the resultant mixture. 11.8G of benzophenone dichloride mixed with 20 ml of dichloromethane was added in dropwise and stirred for four(4) hours at room temperature.

The resultant solution was then cooled to 0° C. and 20 ml of distilled water was added thereto and stirred. The resultant solution was filtrated by using glass filter, washed with dichloromethane, methanol, tetrahydrofuran(THF), 1N HCl, tetrahydrofuran(THF), dichloromethane and methanol, in turns and evaporated in vacuo to give 7.0 g of tritylated alcohol polystyrene resin.

EXAMPLE 7
Preparation of 2-chlorotritylated alcohol polystyrene resin 100.0G of spherical polystyrene resin crosslinked with 1 wt % of divinylbenzene and 1l of dichloromethane were placed in a 3L 4 neck flask in which a mechanical stirrer and a thermometer were installed.

A solution of 167 g of $AlCl_3$ in 0.5L of nitrobenzene was added with stirring the resultant mixture. 334 g of 2-chlorobenzophenone dichloride mixed with 0.5L of dichloromethane was added dropwise and stirred for four(4) hours at room temperature.

The following procedures were identical to those described in Example 6 and 190 g of 2-chlorotritylated alcohol polystyrene resin was obtained thereby.

EXAMPLE 8
Preparation of 4-chlorotritylated alcohol polystyrene resin 7.0G of spherical polystyrene resin crosslinked with 1 wt % of divinylbenzene and 70 ml of dichloromethane were placed in a 250 ml 3 neck flask in which a mechanical stirrer and a thermometer were installed.

A solution of 11.7 g of $AlCl_3$ in 25 ml of carbon bisulfide was added with stirring the resultant mixture. 24 g of 4-chlorobenzophenone dichloride mixed with 30 ml of dichloromethane was added dropwise. The following procedures were identical to those described in Example 6 and 16 g of 4-chlorotritylated alcohol polystyrene resin was obtained thereby.

EXAMPLE 9
Preparation of 4-methyltritylated alcohol polystyrene resin 7.0G of spherical polystyrene resin crosslinked with 1 wt % of divinylbenzene and 70 ml of dichloromethane were placed in a 250 ml 3 neck flask in which a mechanical stirrer and a thermometer were installed.

A solution of 12 g of $AlCl_3$ in 30 ml of nitromethane was added with stirring the resultant mixture. 23 g of 4-methylbenzophenone dichloride mixed with 30 ml of dichloromethane was added dropwise. The following procedures were identical to those described in Example 6 and 11 g of 4-methyltritylated alcohol polystyrene resin was obtained thereby.

EXAMPLE 10
Preparation of 4-methoxytritylated alcohol polystyrene resin 3.0G of spherical polystyrene resin crosslinked with 1 wt % of divinylbenzene and 30 ml of dichloromethane were placed in a 250 ml 3 neck flask in which a mechanical stirrer and a thermometer were installed.

A solution of 5.3 g of $AlCl_3$ in 15 ml of carbon disulfide was added with stirring the resultant mixture. 11 g of 4-methoxybenzophenone dichloride mixed with 15 ml of dichloromethane was added dropwise. The following procedures were identical to those described in Example 6 and as a result, 6 g of 4-methoxyltritylated alcohol polystyrene resin were obtained.

EXAMPLE 11
Preparation of 2-chlorotritylated alcohol polystyrene resin

The procedures were identical to those described in Example 7 except that the reaction solvent was changed from dichloromethane to 1,2-dichloroethane. The resultant mixture was washed and evaporated in vacuo by the method described in Example 7 to give 174 g of 2-chlorotritylated alcohol polystyrene resin.

EXAMPLE 12
Preparation of 2-chlorotritylated alcohol polystyrene resin

The procedures were identical to those described in Example 7 except that the reaction solvent was changed from dichloromethane to chloroform. The resultant mixture was washed and evaporated in vacuo by the method described in Example 7 to give 185 g of 2-chlorotritylated alcohol polystyrene resin.

EXAMPLE 13
Preparation of 2-chlorotritylated alcohol polystyrene resin

The procedures were identical to those described in Example 7 except that the reaction solvent was changed from dichloromethane to 1,2-dichlorobenzene. The resultant mixture was washed and evaporated in vacuo by the method described in Example 7 to give 180 g of 2-chlorotritylated alcohol polystyrene resin.

EXAMPLE 14
Preparation of 2-chlorotritylated alcohol polystyrene resin

The procedures were identical to those described in Example 7 except that the catalyst was changed from $AlCl_3$ to 177 g(158 ml) of $BF_3$ etherate. The resultant mixture was washed and evaporated in vacuo by the method described in Example 7 to give 175 g of 2-chlorotritylated alcohol polystyrene resin.

EXAMPLE 15
Preparation of 2-chlorotritylated alcohol polystyrene resin

The procedures were identical to those described in Example 7 except that the catalyst was changed from $AlCl_3$ to 188 g (111 ml) of trifluoromethane sulfonic acid. The resultant mixture was washed and evaporated in vacuo by the method described in Example 7 to give 182 g of 2-chlorotritylated alcohol polystyrene resin.

EXAMPLE 16
Preparation of 2-chlorotritylated alcohol polystyrene resin

The procedures were identical to those described in Example 7 except that the catalyst was changed from $AlCl_3$ to 123 g(67 ml)of $c.H_2SO_4$. The resultant mixture was washed and evaporated in vacuo by the method described in Example 7 to give 170 g of 2-chlorotritylated alcohol polystyrene resin.

EXAMPLE 17
Preparation of 2-chlorotritylated alcohol polystyrene resin 100G of spherical polystyrene resin crosslinked with 1 wt % of divinylbenzene and 1L of dichloromethane were placed in a 3L 4 neck flask in which a mechanical stirrer and a thermometer were installed.

110 Ml of $SnCl_4$ was added with stirring the resultant mixture. 334 g of 2-chlorobenzophenone dichloride mixed with 0.5L of dichloromethane was added dropwise followed by stirring for eight(8) hours at 40° C. The following washing procedures were identical to those described in Example 7. The cleaned resin was evaporated in vacuo to give 145 g of 2-chlorotritylated alcohol polystyrene resin.

EXAMPLE 18
Preparation of 2-chlorotritylated chloride polystyrene resin 160G of 2-chlorotritylated alcohol polystyrene resin and 1.5l of dried dichloromethane were placed in a 3L 4 neck flask in which a mechanical stirrer and a thermometer were installed. 39 Ml of $SOCl_2$ were added with stirring the resultant mixture followed by stirring for two(2) hours at room temperature. The resultant resin was filtrated by using glass filter, washed with dried dichloromethane and evaporated in vacuo to give 165 g of 2-chlorotritylated chloride polystyrene resin.

EXAMPLE 19
Preparation of Fmoc(9-flourenylmethyloxy carbonyl)-Leu-OH-bonded 2-chlorotritylated polystyrene resin 20G of 2-chlorotritylated chloride polystyrene resin, 7.78 g of Fmoc-Leu-OH, 400 ml of dichloromethane and 15.3 ml of diisopropyl ethylamine were placed in a 1L 3 neck round bottom flask in which a mechanical stirrer and a thermometer were installed and stirred for two(2) hours at room temperature.

The resultant resin was filtrated by using glass filter, washed with dichloromethane, N,N-dimethylformamide, dichloromethane and methanol, in turns and then evaporated in vacuo to give 26.7 g of Fmoc-Leu-OH-bonded 2-chlorotritylated polystyrene resin.

Fmoc-Leu-OH-bonded 2-chlorotritylated polystyrene resin was treated with 20% piperidine/N,N-dimethylformamide(DMF) for 30 minutes.

The substition reaction rate of the resin was then calculated by measuring the UV absorbency of the resultant dibenzofulvene-piperidine adduct at 301 nm.

Fmoc-Leu-OH was bonded to tritylated polystyrene resins having other substituents by the method described above. Each substitution reaction rate was described in Table 1.

TABLE 1

| Tritylated polystyrene resin | The substitutive rate of each Fmoc-Leu-OH-bonded tritylated polystyrene resin |
| --- | --- |
| 4a | 0.60 mmol/g |
| 4b | 0.75 mmol/g |
| 4c | 0.68 mmol/g |
| 4d | 0.74 mmol/g |
| 4e | 0.57 mmol/g |

The present invention provides a process for preparing tritylated polystyrene resin, which requires less production cost and can be controlled easily.

As described in the above, tritylated polystyrene resin can be produce in large scale through more safe and cost effective procedure by the present invention.

What is claimed is:

1. A process for preparing tritylated polystyrene resin(III), comprising a step for tritylating polystyrene by reacting polystyrene resin(II) with benzophenone dihalide(I):

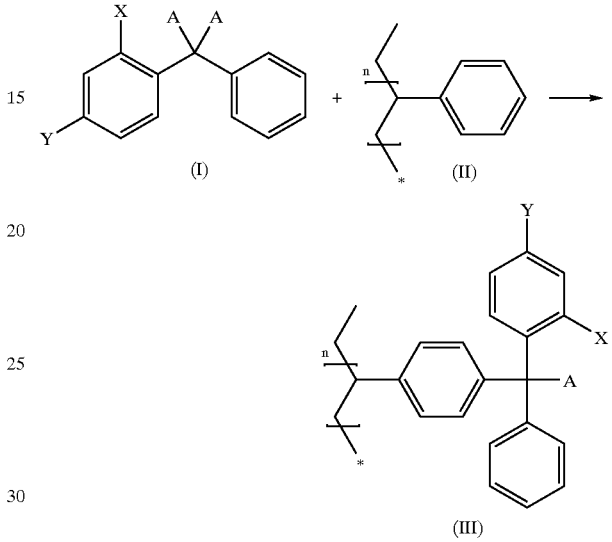

Wherein

X is hydrogen or halogen;

Y is hydrogen, halogen, $C_{1-4}$ alkyl or alkoxy; and

A is halogen.

2. The process for preparing tritylated polystyrene resin (III) according to claim 1, wherein X is Cl.

3. The process for preparing tritylated polystyrene resin (III) according to claim 1, wherein Y is chlorine.

4. The process for preparing tritylated polystyrene resin (III) according to claim 1, wherein Y is methyl.

5. The process for preparing tritylated polystyrene resin (III) according to claim 1, wherein Y is methoxy.

6. The process for preparing tritylated polystyrene resin (III) according to claim 1, wherein said reaction is proceeded in the presence of a Lewis acid catalyst.

7. The process for preparing tritylated polystyrene resin (III) according to claim 6, wherein said Lewis acid catalyst is selected from the group consisting of $AlBr_3$, $AlCl_3$, $BCl_3$, $BF_3$, $BiCl_3$, $GaCl_3$, $FeCl_3$, $SbCl_3$, $SbCl_5$, $SnCl_4$, $TeCl_4$, $ZnCl_2$, $ZrCl_4$, trifluoromethane sulfonic acid and $c.H_2SO_4$.

8. The process for preparing tritylated polystyrene resin (III) according to claim 1, wherein said reaction further comprises a solvent selected from the group consisting of dichloromethane, chloroform, carbon tetrachloride, 1,2-dichloroethane, o-dichlorobenzene, m-dichlorobenzene, p-dichlorobenzene, nitromethane, nitrobenzene, and mixtures thereof.

* * * * *